United States Patent
Pan et al.

(10) Patent No.: US 10,472,616 B2
(45) Date of Patent: Nov. 12, 2019

(54) GENES ENCODING ALPHA-1,3-GLUCANASE AND METHODS OF USING THE SAME

(71) Applicant: GENOFOCUS CO., LTD., Daejeon (KR)

(72) Inventors: Jae Gu Pan, Sejong-si (KR); Eui Joong Kim, Daejeon (KR); Taek Ho Yang, Daejeon (KR); Dong Beom Lee, Daejeon (KR); Eun Young Kim, Daejeon (KR); Hye Rim Lee, Daejeon (KR); Jung Hyun Kang, Daejeon (KR)

(73) Assignee: GENOFOCUS CO., LTD., Daejeon (KR)

( * ) Notice: Subject to any disclaimer, the term of this patent is extended or adjusted under 35 U.S.C. 154(b) by 0 days.

(21) Appl. No.: 15/742,646

(22) PCT Filed: Jul. 15, 2016

(86) PCT No.: PCT/KR2016/007703
§ 371 (c)(1),
(2) Date: Jan. 8, 2018

(87) PCT Pub. No.: WO2017/010833
PCT Pub. Date: Jan. 19, 2017

(65) Prior Publication Data
US 2018/0201914 A1    Jul. 19, 2018

(30) Foreign Application Priority Data
Jul. 15, 2015    (KR) .................. 10-2015-0100592

(51) Int. Cl.
| | |
|---|---|
| *C12N 9/96* | (2006.01) |
| *C12N 9/24* | (2006.01) |
| *A61K 8/66* | (2006.01) |
| *A61Q 11/00* | (2006.01) |

(52) U.S. Cl.
CPC .............. *C12N 9/2405* (2013.01); *A61K 8/66* (2013.01); *A61Q 11/00* (2013.01)

(58) Field of Classification Search
None
See application file for complete search history.

(56) References Cited

U.S. PATENT DOCUMENTS

| 4,438,093 A | 3/1984 | Shimada et al. |
| 2014/0234231 A1 | 8/2014 | Kim et al. |

FOREIGN PATENT DOCUMENTS

| EP | 0307247 A2 | 3/1989 |
| JP | 52-38113 B | 9/1977 |
| JP | 63301788 A | 12/1988 |
| KR | 10-1377071 B1 | 4/2014 |
| WO | 9108291 A2 | 6/1991 |
| WO | 9739114 A1 | 10/1997 |

OTHER PUBLICATIONS

Tilburn, J., et al, "Transformation by Integration in Aspergillus Nidulans", "Gene", 1983, pp. 205-221, vol. 26.
Hasegawa, S., et al., "Enzymes That Hydrolyze Fungal Cell Wall Polysaccharides", "The Journal of Biological Chemistry", Oct. 25, 1969, pp. 5460-5470, vol. 244, No. 20.
Pleszczynska, M., et al., "Mutanase from *Paenibacillus* sp. MP-1 produced inductively by fungal a-1,3-glucan and its potential for the degradation of mutan and *Streptococcus mutans* biofilm", "Biotechnology Letters", Jul. 11, 2010, pp. 1699-1704, vol. 32.
Takehara, T., et al., "Purification and Properties of Endo-a-1,3-Glucanase from a Streptomyces chartreusis Strain", "Journal of Bacteriology", Feb. 1981, pp. 729-735, vol. 145, No. 2.
Van Munster, J. M., et al., "Characterization of the starvation-induced chitinase CfcA and a-1,3-glucanase AgnB of Aspergillus niger", "Applied Microbiology and Biotechnology", Sep. 16, 2014, pp. 2209-2223, vol. 99.
Walker, G. J., et al., "Metabolism of the Polysaccharides of Human Dental Plaque", "Carbohydrate Research", Oct. 1977, pp. 415-432, vol. 58, No. 2.

*Primary Examiner* — Hope A Robinson
(74) *Attorney, Agent, or Firm* — Hultquist, PLLC; Steven J. Hultquist

(57) ABSTRACT

The present invention relates to a novel alpha-1,3-glucanase, and more particularly, to a novel alpha-1,3-glucanase from *Trichoderma harzianum*, a gene encoding the same, a recombinant vector and recombinant microorganism comprising the gene, and a method of producing an alpha-1,3-glucanase using the recombinant microorganism. The novel alpha-1,3-glucanase according to the present invention can effectively degrade mutan, which is a component of a microbial biofilm, and thus it can be used in oral hygiene products and the medical field.

5 Claims, 1 Drawing Sheet
(1 of 1 Drawing Sheet(s) Filed in Color)
Specification includes a Sequence Listing.

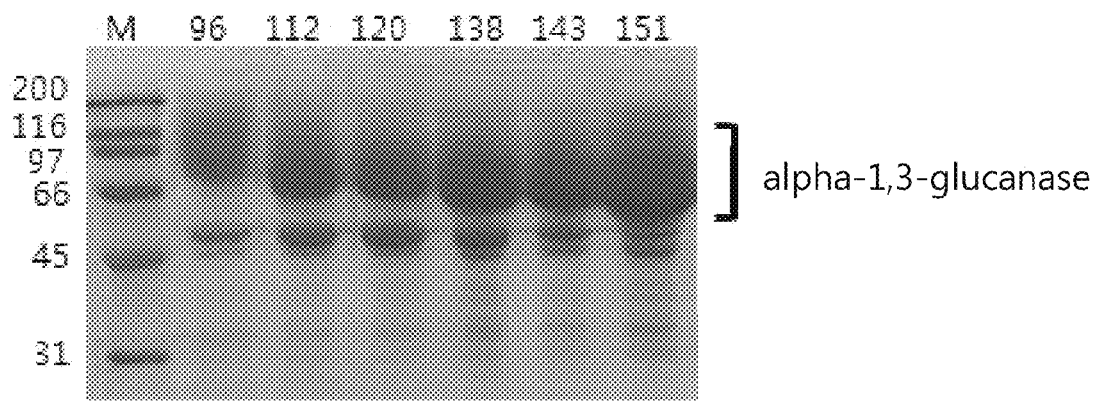

GENES ENCODING ALPHA-1,3-GLUCANASE AND METHODS OF USING THE SAME

CROSS-REFERENCE TO RELATED APPLICATIONS

This application is a U.S. national phase under the provisions of 35 U.S.C. § 371 of International Patent Application No. PCT/KR2016/007703 filed Jul. 15, 2016, which in turn claims priority of Korean Patent Application No. 10-2015-0100592 filed Jul. 15, 2015. The disclosures of such international patent application and Korean priority patent application are hereby incorporated herein by reference in their respective entireties, for all purposes.

TECHNICAL FIELD

The present invention relates to a novel alpha-1,3-glucanase, and more particularly to a novel alpha-1,3-glucanase from *Trichoderma harzianum*, a gene encoding the same, a recombinant vector and a recombinant microorganism containing the gene, and a method of producing an alpha-1,3-glucanase using the recombinant microorganism.

BACKGROUND ART

*Streptococcus mutans* is a microorganism that plays an important role in plaque formation in the oral cavity and is known to be most closely associated with tooth decay. The microorganism has the ability to degrade sugar to synthesize insoluble glucan in the extracellular matrix. The synthesized glucan is a sugar polymer having both a α-1,6 bond and a α-1,3 bond, forms a biofilm on the tooth surface due to its high stickiness and water insolubility, facilitates the adhesion of *Streptococcus mutans*, and aggregates various bacteria. Organic acids that are produced in this biofilm by adhesion of *Streptococcus mutans* and the like cause demineralization of tooth enamel or tissue to cause tooth decay. In addition, it is known that the formed biofilm also plays a major role in the development and progression of periodontitis.

Dental plaque comprises glucans that are polymers of glucose, and fructans that are polymers of fructose. Glucans are divided into three types: dextran having an alpha-1,6-glucose bond alone; a water-soluble glucan having an alpha-1,6-glucose bond as a main bond; and water-insoluble glucan (i.e., mutan) having an alpha-1,3-glucose bond as a main bond (Rolla et al., 1985). Mutan that is produced by *Streptococcus mutans* bacteria comprises 80-90% alpha-1, 3-glucose bond and the remainder being an alpha-1,6-glucose bond.

Dextranase degrades the alpha-1,6-glucose bond of dental plaque. Known dextranase genes of fungal origin include genes from *Penicillium, Paecilomyces, Aspergillus, Fusarium, Spicaria, Verticillium, Helminthosporium, Chaetomium*, and the like, and known dextranase genes of bacterial origin include genes from *Lactobacillus, Streptococcus, Cellvibrio, Cytophaga, Brevibacterium, Pseudomonas, Corynebacterium, Arthrobacter, Flavobacterium*, and the like.

In foreign countries, Amano Co., Ltd. which is a Japanese enzyme company has launched a dextranase product derived from *Paecilomyces lilacinus*. The dextranase product is used mainly to remove dextran which is produced by contaminant bacteria in a process of producing sugar from sugarcane, and it is also used in some oral products.

Clinica Lion (product name) commercially available from Lion Co., Ltd. (Japan) also comprises dextranase containing triclosan. Although triclosan can temporally reduce *Streptococcus mutans*, it is expected that the dextranase enzyme alone will have an insufficient ability to degrade dental plaque.

In Korea, novel dextranase from Kimchi lactic acid bacteria was developed, and a toothpaste comprising dextranase and glucose oxidase was launched. However, they were not commercially successful, because the effect of dextranase on biofilm degradation is insufficient.

Alpha-1,3-glucanase is an enzyme that degrades the alpha-1,3-glucose bond of dental plaque and is also called mutanase. Enzymes that degrade alpha-1,3-glucose bonds have been found in *Trichoderma* sp. (Hasegawa et al., J. Biol. Chem., 244: 5460-5470, 1969), *Streptomyces* (Takehara et al., J Bacteriol., 145:729-735, 1981), *Cladosporium resinae* (Hare et al. Carbohydr Res., 58:415-432, 1977), *Pseudomonas* sp. (U.S. Pat. No. 4,438,093), *Flavobacterium* sp. (Japanese Patent No. 77038113), *Bacillus circulanse* (Japanese Patent No. 63301788), *Aspergillus* sp., and the like. However, studies on the ability to degrade mutan in the oral cavity remain at an early stage. Alpha-1,3-glucanase was developed overseas but was not commercialized due to its low mutan-degrading activity. Recently, alpha-1,3-glucanase from *Bacillus circulans* was developed in Japan and has been supplied to GlaxoSmithKline (GSK), Inc. and applied to Biotene mouthwashes and toothpaste products. However, the enzyme has not been launched as a product.

Accordingly, the present inventors have made extensive efforts to develop an enzyme having an excellent effect of degrading bacterial biofilms, and as a result, have found that novel alpha-1,3-glucanase from *Trichoderma harzianum* strain GF101 exhibits a high effect on biofilm degradation, thereby completing the present invention.

DISCLOSURE OF INVENTION

Technical Problem

It is an object of the present invention to provide a novel alpha-1,3-glucanase having an excellent effect on degrading bacterial biofilms.

Another object of the present invention is to provide a gene encoding the novel alpha-1,3-glucanase and a recombinant vector comprising the gene.

Still another object of the present invention is to provide a recombinant microorganism into which the gene or the recombinant vector is introduced and a method for producing an alpha-1,3-glucanase using the recombinant microorganism.

Yet another object of the present invention is to provide a method for degrading a biofilm produced by *Streptococcus* sp. strain using the alpha-1,3-glucanase.

Technical Solution

To achieve the above objects, the present invention provides an alpha-1,3-glucanase having an amino acid sequence of SEQ ID NO: 1.

The present invention also provides a gene encoding the alpha-1,3-glucanase and a recombinant vector comprising the gene.

The present invention also provides a recombinant microorganism into which the gene or the recombinant vector is introduced.

The present invention also provides a method for producing alpha-1,3-glucanase, the method comprising the steps of (a) producing alpha-1,3-glucanase by culturing the recombinant microorganism; and (b) obtaining the produced alpha-1,3-glucanase.

The present invention also provides a method for degrading a biofilm using the alpha-1,3-glucanase.

The present invention also provides a method for degrading a biofilm using the alpha-1,3-glucanase.

The present invention also provides an oral hygiene product comprising the alpha-1,3-glucanase.

BRIEF DESCRIPTION OF THE DRAWING

The patent or application file contains at least one drawing executed in color. Copies of this patent or patent application publication with color drawing(s) will be provided by the Office upon request and payment of the necessary fee.

FIG. 1 shows the results of culture time-dependent SDS-PAGE analysis performed to examine the protein expression pattern of a recombinant alpha-1,3-glucanase produced in *Aspergillus niger* transformed with a recombinant alpha-1,3-glucanase gene (M: protein size marker (Bio-rad: 161-0317); 200: myosin; 116: beta-galactosidase; 97: phosphorylase b; 66: serum albumin; 45: ovalbumin; and 31: carbonic anhydrase).

BEST MODE FOR CARRYING OUT THE INVENTION

Unless defined otherwise, all the technical and scientific terms used herein have the same meaning as those generally understood by one of ordinary skill in the art to which the invention pertains. Generally, the nomenclature used herein and the experiment methods, which will be described below, are those well known and commonly employed in the art.

The present inventors have conducted studies on the production of recombinant proteins using fungi, and as a result, have developed a fungal cell wall degrading enzyme for transformation. A number of strains producing an enzyme that degrades glucan which is the major component of the fungal cell wall were screened, and among these strains, a *Trichoderma* sp. strain having a relatively high enzyme secretion activity was selected (*Trichoderma* sp. GF01). The results of rRNA analysis revealed that the GF101 strain is *Trichoderma harzianum*. It was found that glucan-degrading enzymes secreted from the *Trichoderma harzianum* GF101 strain include alpha-1,3-glucanase, beta-1,3-glucanase, exo-beta-1,4-glucanase, endo-beta-1,4-glucanase, beta-1,4-glucosidase, kininase and protease, and among these enzymes, alpha-1,3-glucanase is most abundant.

The present inventors analyzed the N-terminal amino acid sequence, and as a result, found that the N-terminal amino acid sequence is ASSADRLVFC which is 100% identical to that of an alpha-1,3-glucanase from *Trichoderma harzianum*. In an example of the present invention, the nucleotide sequence of the alpha-1,3-glucanase from *Trichoderma harzianum* was analyzed, and the alpha-1,3-glucanase was produced in *Aspergillus niger*.

Therefore, in one aspect, the present invention is directed to an alpha-1,3-glucanase having the amino acid sequence of SEQ ID NO: 1.

In the present invention, a novel alpha-1,3-glucanase gene was isolated from the *Trichoderma harzianum* GF101 genome. The isolated alpha-1,3-glucanase showed homologies of 98%, 99% and 99% to the alpha-1,3-glucanases from known *T. harzianum* CECT2413, CCM-F340 and CBS243.71, respectively.

The alpha-1,3-glucanase of the present invention has a signal peptide (SEQ ID NO: 1; underlined) consisting of 24 amino acids at the N-terminal end and thus is extracellularly secreted. In addition, it has a propeptide (SEQ ID NO: 1; italics) consisting of 13 amino acids at the N-terminal end. The active portion of the alpha-1,3-glucanase, excluding the signal peptide and the propeptide, consists of 599 amino acids and has a molecular weight of 63.9 kD.

In another aspect, the present invention is directed to a gene encoding the alpha-1,3-glucanase.

The nucleotide sequence of the novel alpha-1,3-glucanase gDNA gene is represented by SEQ ID NO: 3, and the gDNA comprising the alpha-1,3-glucanase gene is 2069 bp in total length and consists of three introns (SEQ ID NO: 2; underlined). In addition, the nucleotide sequence of the cDNA gene, excluding introns, is represented by SEQ ID NO: 3, is 1908 bp in length and encodes 636 amino acids.

TABLE 1

Amino acid and nucleotide sequences of alpha-1,3-glucanase

| SEQ ID NO: | Remarks | Sequences |
| --- | --- | --- |
| SEQ ID NO: 1 | Amino acid sequence | mlqvfrrlqlqalaaaalsslqsaapanvairsleerassadrlvfchfmigivgdrgssadyd ddmqrakaagidafalnigvdgytdqqlgyaydsadrngmkvfisfdfnwwspgnavg vgqkiaqyanrpaqlyvdnrpfassfagdgldvnalrsaagsnvyfvpnfhpgqsspsnid galnwmawdndgnnkapkpgqtvtvadgdnayknwlggkpylapvspwffthfgpe vsysknwvfpggpliynrwqqvlqqgfpmveivtwndygeshyvgplkskhfddgns kwvndmphdgfldlskpfiaayknrdtdiskyvqneqlvywyrrnlkaldcdatdasnrp anngsgnyfmgrpdgwqtmddtvyvaalllktagsvtvtsggttqtfqanaganlfqipasi gqqkfaltrngqtvfsgtslmditnvcscgiynfnpyvgtipagfddplqadglfsltiglhvtt cqakpslgtnppvtsgpvsslpassttrassppppvsstrvssppvssppvsrtssappppasst ppsgqvcvagtvadgesgnyiglcqfscnygycppgpckctafgapisppasngrngcpl pgegdgylglcsfscnhnycpptacqyc |
| SEQ ID NO: 2 | gDNA sequence | atgttgggcgttttccgccgcctcgggctgggcgccctagctgccgcagctctatcttctctcgg cagtgccgctcccgccaatgttgctatccggtctctcgaggagcgcgcttcctctgctgaccgtc ttgtattctgtcacttcat<u>ggttagtttttacctaggaattataaggatgaggactaatgtagcaacgt catgacag</u>attggtatcgttggtgaccgtggcagctcggcagattatgatgacgatatgcaacgt gccaaagccgctggcattgacgccttcgccctgaacatcggcgttgacggctataccgaccag cagctcggctatgcctatgactctgccgatcgtaatggcatgaaagtcttcatttcatttgatttcaa ctggtggagccccggcaatgcagttggtgttggccagaagattgcgcagtatgccaaccgccc |

TABLE 1-continued

Amino acid and nucleotide sequences of alpha-1,3-glucanase

| SEQ ID NO: | Remarks | Sequences |
|---|---|---|
| | | tgcccagctgtatgtcgacaaccggccattcgcctcttccttcgccggtgacggtctggatgtaa
atgcgttgcgctctgctgcaggctccaacgtttactttgtgcccaacttccaccctggtcaatcttc
cccctccaacattgatggcgcccttaactggatggtaagccgcaactccagagccgagagtag
gaaagcaatactaatgtgtttttagtccagtttctcgcacctcttctgccctcccccctccggccag
cagcacgccgccatcgggtcaggtttgcgttgccggcaccgttgccgacggcgagtctggca
actacatcggcctgtgccaattcagctgcaagtaggttgcccccataccccttacttgcttccttaa
ctaatcctagtagctacggttactgcccaccaggaccgtgtaagtgcaccgcctaggtgctccc
atctcgccaccggcatccaacggccgcaacggctgccctctgccgggagaaggcgatggtta
tctgggcctgtgcagtttcagttgtaaccataattactgcccgccaacggcatgtcaatactgcta
g |
| SEQ ID NO: 3 | cDNA sequence | gaaggcattggactgcgacgccaccgacaccacctctaaccgcccggctaacaatggaagcg
gtaattactttatgggacgccctgatggttggcaaactatggatgacaccgtttatgttgccgcact
tctcaagactgccggtagcgtcacggtcacgtctggtggcaccactcaaacgttccaggccaa
cgccggagccaatctcttccaaatcccggccagcatcggccagcaaaagtttgctctgactcgt
aacggtcagaccgtctttagcggaacctcattgatggatatcaccaacgtttgctcttgcggtatct
acaacttcaacccatatgttggcaccattcctgccggctttgacgccctcttcaggctgacggtc
ttttctctttgaccatcggattgcacgtcacaacttgtcaggccaagccatctcttggaactaaccc
tcctgtcacttccggccctgtgtcctcgcttccagcttcctccaccaccgcgcatcctcgccgcc
tcctgtttcttcaactcgtgtctcttctccccctgtctcttccccctccagtttctcgcacctcttctgccc
ctcccctccggccagcagcacgccgccatcgggtcaggtttgcgttgccggcaccgttgccg
acggcgagtctggcaactacatcggcctgtgccaattcagctgcaactacggttactgcccacc
aggaccgtgtaagtgcaccgcctttggtgctcccatctcgccaccggcatccaacggccgcaa
cggctgccctctgccgggagaaggcgatggttatctgggcctgtgcagtttcagttgtaaccata
attactgcccgccaacggcatgtcaatactgctag |

In still another aspect, the present invention is directed to a recombinant vector comprising the gene encoding the alpha-1,3-glucanase and a recombinant microorganism into which the gene encoding the alpha-1,3-glucanase or the recombinant vector is introduced.

In the present invention, the recombinant microorganism may be selected from the group consisting of bacteria, fungi, and yeasts.

In an example of the present invention, recombinant *E. coli* transformed with the gene encoding the alpha-1,3-glucanase was produced, and in another example, fungus *Aspergillus niger* transformed with the gene encoding the alpha-1,3-glucanase was produced.

It was found that, in the case of the alpha-1,3-glucanase produced by the *Aspergillus niger* transformant produced in one example of the present invention, the original molecular weight of the protein is 64.9 kD, but the molecular weight of the protein after glycosylation varies in the range of 115 to 240 kD.

As used herein, the term "vector" means a DNA construct containing a DNA sequence operably linked to a suitable control sequence capable of effecting the expression of the DNA in a suitable host. The vector may be a plasmid, a phage particle, or simply a potential genomic insert. Once incorporated into a suitable host, the vector may replicate and function independently of the host genome, or may in some instances, integrate into the genome itself. In the present specification, "plasmid" and "vector" are sometimes used interchangeably, as the plasmid is the most commonly used form of vector. However, the present invention is intended to include other types of vectors with the same function as that would be known or known in the art. Typical expression vectors for mammalian cell culture expression are based on, for example, pRK5 (EP 307,247), pSV16B (WO91/08291), and pVL1392 (Pharmingen).

As used herein, the term "expression control sequence" refers to the DNA sequences essential for the expression of the coding sequence operably linked in a particular host organism. Such control sequences include a promoter for performing transcription, any operator sequence for controlling such transcription, a sequence for encoding a suitable mRNA ribosomal binding site, and a sequence for controlling the termination of transcription and translation. For example, control sequences suitable for prokaryotes include a promoter, an operator sequence, and a ribosomal binding site. Eukaryotic cells include promoters, polyadenylation signals, and enhancers. The factor having the greatest effect on the expression level of the gene in the plasmid is a promoter. SRα promoter, cytomegalovirus promoter and the like are preferably used as a promoter for high expression.

To express the DNA sequence of the present invention, any of a wide variety of expression control sequences may be used in the vector. Examples of useful expression control sequences include, for example, the early and late promoters of SV40 or adenovirus, the lac system, the trp system, the TAC or TRC system, T7 or T3 promoter, the major operator and promoter regions of phage lambda, the control regions of fd coat protein, the promoter for 3-phosphoglycerate kinase or other glycolytic enzymes, the promoters of said-phosphatase, the promoters of the yeast α-mating system, and other sequences known to control the expression of genes of prokaryotic or eukaryotic cells or their viruses, and various combinations thereof. T7 RNA polymerase promoter Φ10 may be effectively used to express the desired protein in *E. coli*.

A nucleic acid is operably linked when it is placed in a functional relationship with another nucleic acid sequence. The nucleotide sequence may be a gene and a control sequence(s) linked to being capable of expressing the gene when a proper molecule (e.g., transcription-activating protein) binds to a control sequence(s). For example, DNA for a pre-sequence or a secretory leader is operably linked to DNA encoding polypeptide when expressed as pre-protein participating in secretion of polypeptide; a promoter or an enhancer is operably linked to a coding sequence when affecting the transcription of the sequence; and an RBS is operably linked to a coding sequence when affecting the transcription of the sequence, or to a coding sequence when arranged to facilitate translation. Generally, the term "operably linked" means that the DNA linked sequences are contiguous, and in the case of the secretory leader, are contiguous and present in a reading frame. However, an enhancer is not necessarily contiguous. The linkage between these sequences is performed by ligation at a convenient restriction enzyme site. However, when the site does not exist, a synthetic oligonucleotide adaptor or a linker is used according to a conventional method.

The term "expression vector" as used herein generally means a double-stranded DNA fragment functioning as a recombinant carrier into which a heterologous DNA fragment is inserted. Here, the heterologous DNA means a hetero-type DNA, which is not naturally found in a host cell. The expression vector may be self-replicable regardless of host chromosomal DNA once in a host cell and may produce several copies of the vector and (heterologous) DNA inserted thereinto.

As is well known in the art, in order to increase the expression level of a transfected gene in a host cell, a corresponding gene should be operably linked to transcription and translation expression control sequences which are operated in a selected expression host. Preferably, the expression control sequences and the corresponding gene are included in one expression vector together with a fungal selection marker and a replication origin.

The host cell transformed or transfected by the aforementioned expression vector constitutes another aspect of the present invention. As used herein, the term "transformation" means that DNA can be replicated as a factor outside of chromosome or by means of completion of the entire chromosome by introducing DNA as a host.

As used herein, the term "transfection" means that an expression vector is accepted by a host cell regardless of whether or not any coding sequence is actually expressed. Of course, it should be understood that all vectors and expression control sequences do not equally function to express DNA sequences according to the present invention. Similarly, all hosts do not equally function with respect to the same expression system. However, one skilled in the art may appropriately select from among various vectors, expression control sequences, and hosts without either departing from the scope of the present invention or bearing the excessive experimental burden.

For example, a vector must be selected considering a host cell, because the vector must be replicated in the host cell. Specifically, the copy number of the vector, the ability to regulate the copy number and the expression of other protein encoded by the corresponding vector (e.g., the expression of an antibiotic marker) should also be considered. Also, an expression control sequence may be selected taking several factors into consideration. For example, relative strength, control capacity and compatibility with the DNA sequence of the present invention of the sequence should be deliberated particularly with respect to possible secondary structures. Further, the selection of a single cell host may be made under consideration of compatibility with a selected vector, toxicity of a product encoded by a DNA sequence, secretory nature of the product, ability to correctly fold a polypeptide, fermentation or cultivation requirements, ability to ensure easy purification of a product encoded by a DNA sequence, or the like. Within the scope of these parameters, one of ordinary skill in the art may select various vectors/expression control sequences/host combinations that can express the DNA sequences of the invention in either large-scale animal culture or fermentation. In cloning the cDNA of the desired protein by the expression cloning strategy, screening procedures such as a binding method, a panning method, and a film emulsion method can be used.

In the definition of the present invention, the term "substantially pure" means that a polypeptide according to the present invention and the DNA sequences encoding the polypeptide substantially does not contain any other proteins derived from bacteria.

As host cells for expressing recombinant proteins, procaryotic cells, such as *E. coli* and *Bacillus subtillis*, which can be liquid-cultured, easily genetically modified and have well established genetic and physiological properties, have been widely used. However, to solve various problems, including the post-translational modification, secretion, three-dimensional active structure and activation of proteins, a wide range from microorganisms to higher organisms, including unicellular eukaryotic cells, yeasts (*Pichia pastoris, Saccharomyces cerevisiae, Hansenula polymorpha*, etc.), filamentous fungi, insect cells, plant cells, and mammalian cells, has recently been used as host cells for recombinant protein production. Thus, it will be obvious to one skilled in the art to use not only *Aspergillus niger* illustrated in Examples but also other host cells.

In a further aspect, the present invention is directed to a method for producing alpha-1,3-glucanase, comprising culturing the recombinant microorganism to produce alpha-1,3-glucanase.

In a still further aspect, the present invention is directed to a method for producing alpha-1,3-glucanase, comprising the steps of (a) producing alpha-1,3-glucanase by culturing the recombinant microorganism; and (b) obtaining the produced alpha-1,3-glucanase.

In an example of the present invention, a recombinant alpha-1,3-glucanase was produced using transformed recombinant *A. niger*. The pASP vector (GenoFocus, Korea) used in the production of the recombinant alpha-1,3-glucanase makes it possible to produce the recombinant protein by microbial culture alone without needing to add a special inducer for protein expression in a state in which protein expression is separated from cell growth.

The alpha-1,3-glucanase produced by the above-described method was analyzed by SDS-PAGE, and as a result, a band having a size of 115 to 240 kDa was observed (FIG. 1).

In a yet further aspect, the present invention is directed to a method for degrading a biofilm using the alpha-1,3-glucanase.

In one example of the present invention, it was shown that when mutan produced by *Streptococcus mutans* was treated with the enzyme from *Aspergillus niger*, reducing sugar was formed by mutan degradation.

In still another further aspect, the present invention is directed to an oral hygiene product containing the alpha-1,3-glucanase.

In the present invention, the oral hygiene product may be a toothpaste or a mouthwash.

EXAMPLES

Hereinafter, the present invention will be described in further detail with reference to examples. It will be obvious to a person having ordinary skill in the art that these examples are for illustrative purposes only and are not to be construed to limit the scope of the present invention.

Example 1: Cloning of Novel Alpha-1,3-Glucanase from *Trichoderma*

Using the nucleotide sequence of the novel alpha-1,3-glucanase gene from *Trichoderma harzianum*, a recombinant vector and a recombinant microorganism were constructed. Based on the nucleotide sequence of an alpha-1,3-glucanase gene of SEQ ID NO: 2, a MutF primer of SEQ ID NO: 4 and a MutR primer of SEQ ID NO: 5 were constructed.

```
SEQ ID NO: 4 MutF:
atataggcctatgttgggcgttttccgccgcctc

SEQ ID NO: 5 MutR:
atatgcggccgcctagcagtattgacatgccgttgg
```

Using the genomic gDNA of *Trichoderma harzianum* GF101 as a template, PCR was performed using MutF and MutR primers. The PCR product was purified, and then digested with the restriction enzymes StuI and NotI inserted in the primers, after which it was inserted into the same restriction enzyme sites of a pASP vector (GenoFocus, Korea), thereby constructing a vector named pASPGFMUT. The constructed vector was transformed into an *E. coli* DH5a strain.

Example 2: Production of Recombinant Vector and Recombinant Microorganism Containing Alpha-1,3-Glucanase Gene From the recombinant *E. coli* strain constructed in Example 1, pASPGFMUT plasmid DNA was obtained. The expression vector pASPGFMUT was introduced and transformed into *Aspergillus niger* (Tilburn et al., Gene., 26:205-221, 1983).

For transformation, a mycelium cultured in liquid YPD (Yeast extract 1%, peptone 2%, Dextran 2%) medium for 15 hours was treated with cell wall-degrading enzyme (Sigma L1412) to prepare a protoplast, and then the pASPGFMUT DNA was inserted into the genome. For screening, recombinant microorganisms were screened on YPD agar medium containing 100 μg/ml of hygromycin B and were subcultured.

Example 3: Flask Culture of Recombinant Microorganisms

Among the recombinant microorganisms obtained in Example 2, recombinant microorganisms having resistance to hygromycin B were spot-inoculated on the same agar medium and subcultured for one passage. After 4 days, recombinant microorganism spores were distributed uniformly on agar complete medium, and then cultured at 30° C. for 5-6 days until spores were formed uniformly.

From the culture dish incubated for 5 days, asexual spores were harvested with 0.1% Tween 80 at a density of $1 \times 10^6$ cells/ml, and 1 ml of a dilution of the asexual spores was inoculated into 50 ml of liquid production medium (Glucose 5% soybean meal 2% CSL1%). After inoculation, the cells were cultured in a shaking incubator at 200 rpm and 28° C. for 4 days or more. The culture was centrifuged at 10,000 g for 10 minutes to remove the cells, and the collected culture supernatant was subjected to protein electrophoresis (SDS-PAGE).

The results of the electrophoresis analysis are shown in FIG. 1. As can be seen therein, the molecular weight of the alpha-1,3-glucanase was 64.9 kD, but the actual size of the alpha-1,3-glucanase after glycosylation varied in the range of 115 to 240 kD. Analysis performed using an O-link glycosylation analysis program (www.cbs.dtu.dk/services/NetOGlyc/) indicated that glycosylation sites are present at positions 316, 317, 446, 452, 455, 460, 461, 465, 466, 470, 471, 472, 473, 477, 482, 483, 484, 487, 488, 492, 493, 497, 499, 500, 501, 508, 509, 510, 558, and 562.

The cells were removed without cell disruption, and the supernatant was electrophoresed. As a result, it could be seen that the alpha-1,3-glucosidase was secreted extracellularly from *Aspergillus niger* by the signal peptide. The secreted liquid fermentation broth showed an activity of 33.6 U/ml. The liquid fermentation broth was added to 5% trehalose and freeze-dried, thereby preparing powder.

Powder, obtained by culturing the recombinant transformant for 151 hours, followed by freeze drying, showed an alpha-1,3-glucanase activity of 105.4 U/g.

Example 4: Measurement of Enzymatic Activity of Alpha-1,3-Glucanase

Using mutan isolated from a culture of *Streptococcus mutans*, the production of free reducing sugar was quantified. 10 mg of mutan was placed in a tube, and 0.9 ml of 0.1 M phosphate buffered saline was added thereto so that the mutan was dispersed uniformly. The solution containing the mutan was allowed to stand at 37° C. for about 5 minutes. 0.1 ml of the fermentation broth or 1 g of the freeze-dried powder, obtained in Example 3, was dissolved in 9 ml of water to obtain an enzyme solution, and 0.1 ml of the enzyme solution was added to the mutan-containing solution to a total volume of 1 ml. The resulting reaction solution was allowed to react at 37° C. for 30 minutes. To deactivate the enzyme, the reaction solution was kept in boiling water for about 3 minutes.

To separate the mutan after the reaction, centrifugation was performed at 12,000 rpm for 10 minutes. For quantification, 0.5 ml of the separated supernatant was used without dilution or after suitable dilution, and the amount of free reducing sugar produced during the reaction was quantified by the Somogyi-Nelson method. The activity of the enzyme is defined as the amount of enzyme that produces free reducing sugar in an amount of 1 μmole per minute.

INDUSTRIAL APPLICABILITY

The novel alpha-1,3-glucanase according to the present invention can effectively degrade mutan, which is a component of a microbial biofilm, and thus it can be used in oral hygiene products and the medical field.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. A recombinant *Aspergillus niger* microorganism transformed with a pASP vector, the vector comprising a nucleotide sequence of SEQ ID NO: 3, wherein the recombinant *Aspergillus niger* microorganism produces a secreted glycosylated alpha-1,3-glucanase comprising the amino acid sequence of SEQ ID NO: 1, wherein the secreted glycosylated alpha-1,3-glucanase has a molecular weight in a range of 115 to 240 kDa, and wherein the secreted glycosylated alpha-1,3-glucanase has enzymatic activity against mutan produced by *Streptococcus mutans*.

2. A method for producing alpha-1,3-glucanase, comprising:
   (a) culturing the recombinant microorganism of claim 1 to secrete glycosylated alpha-1,3-glucanase; and
   (b) removing cells of the recombinant microorganism from the culturing to obtain the glycosylated alpha-1,3-glucanase secreted by the recombinant microorganism.

3. A method for degrading a biofilm, comprising contacting the biofilm with the secreted glycosylated alpha-1,3-glucanase obtained from the *Aspergillus niger* microorganism of claim 1.

4. The method of claim 3, wherein the biofilm is produced by a *Streptococcus* sp. strain.

5. The recombinant *Aspergillus niger* microorganism of claim 1, wherein said secreted glycosylated alpha-1,3-glucanase comprises glycosylation sites at positions 316, 317, 446, 452, 455, 460, 461, 465, 466, 470, 471, 472, 473, 477, 42, 43, 44, 487, 488, 492, 493, 497, 499, 500, 501, 508, 509, 510, 558, and 562.

* * * * *

UNITED STATES PATENT AND TRADEMARK OFFICE
CERTIFICATE OF CORRECTION

PATENT NO. : 10,472,616 B2
APPLICATION NO. : 15/742646
DATED : November 12, 2019
INVENTOR(S) : Jae Gu Pan et al.

Page 1 of 1

It is certified that error appears in the above-identified patent and that said Letters Patent is hereby corrected as shown below:

In the Specification

Column 9, Line 30:
"DH5a"
Should be:
-- DH5α --.

Signed and Sealed this
Twenty-eighth Day of January, 2020

Andrei Iancu
*Director of the United States Patent and Trademark Office*

SEQUENCE LISTING

<160> NUMBER OF SEQ ID NOS: 5

<210> SEQ ID NO 1
<211> LENGTH: 635
<212> TYPE: PRT
<213> ORGANISM: Trichoderma harzianum

<400> SEQUENCE: 1

Met Leu Gly Val Phe Arg Arg Leu Gly Leu Gly Ala Leu Ala Ala Ala
1               5                   10                  15

Ala Leu Ser Ser Leu Gly Ser Ala Ala Pro Ala Asn Val Ala Ile Arg
            20                  25                  30

Ser Leu Glu Glu Arg Ala Ser Ser Ala Asp Arg Leu Val Phe Cys His
        35                  40                  45

Phe Met Ile Gly Ile Val Gly Asp Arg Gly Ser Ser Ala Asp Tyr Asp
    50                  55                  60

Asp Asp Met Gln Arg Ala Lys Ala Ala Gly Ile Asp Ala Phe Ala Leu
65                  70                  75                  80

Asn Ile Gly Val Asp Gly Tyr Thr Asp Gln Gln Leu Gly Tyr Ala Tyr
                85                  90                  95

Asp Ser Ala Asp Arg Asn Gly Met Lys Val Phe Ile Ser Phe Asp Phe
            100                 105                 110

Asn Trp Trp Ser Pro Gly Asn Ala Val Gly Val Gly Gln Lys Ile Ala
        115                 120                 125

Gln Tyr Ala Asn Arg Pro Ala Gln Leu Tyr Val Asp Asn Arg Pro Phe
    130                 135                 140

Ala Ser Ser Phe Ala Gly Asp Gly Leu Asp Val Asn Ala Leu Arg Ser
145                 150                 155                 160

Ala Ala Gly Ser Asn Val Tyr Phe Val Pro Asn Phe His Pro Gly Gln
                165                 170                 175

Ser Ser Pro Ser Asn Ile Asp Gly Ala Leu Asn Trp Met Ala Trp Asp
            180                 185                 190

Asn Asp Gly Asn Asn Lys Ala Pro Lys Pro Gly Gln Thr Val Thr Val
        195                 200                 205

Ala Asp Gly Asp Asn Ala Tyr Lys Asn Trp Leu Gly Gly Lys Pro Tyr
    210                 215                 220

Leu Ala Pro Val Ser Pro Trp Phe Phe Thr His Phe Gly Pro Glu Val
225                 230                 235                 240

Ser Tyr Ser Lys Asn Trp Val Phe Pro Gly Gly Pro Leu Ile Tyr Asn
                245                 250                 255

Arg Trp Gln Gln Val Leu Gln Gly Phe Pro Met Val Glu Ile Val
            260                 265                 270

Thr Trp Asn Asp Tyr Gly Glu Ser His Tyr Val Gly Pro Leu Lys Ser
        275                 280                 285

Lys His Phe Asp Asp Gly Asn Ser Lys Trp Val Asn Asp Met Pro His
    290                 295                 300

Asp Gly Phe Leu Asp Leu Ser Lys Pro Phe Ile Ala Ala Tyr Lys Asn
305                 310                 315                 320

Arg Asp Thr Asp Ile Ser Lys Tyr Val Gln Asn Glu Gln Leu Val Tyr
                325                 330                 335

Trp Tyr Arg Arg Asn Leu Lys Ala Leu Asp Cys Asp Ala Thr Asp Thr
            340                 345                 350

Thr Ser Asn Arg Pro Ala Asn Asn Gly Ser Gly Asn Tyr Phe Met Gly
        355                 360                 365

```
Arg Pro Asp Gly Trp Gln Thr Met Asp Asp Thr Val Tyr Val Ala Ala
    370                 375                 380

Leu Leu Lys Thr Ala Gly Ser Val Thr Val Ser Gly Gly Thr Thr
385                 390                 395                 400

Gln Thr Phe Gln Ala Asn Ala Gly Ala Asn Leu Phe Gln Ile Pro Ala
                405                 410                 415

Ser Ile Gly Gln Gln Lys Phe Ala Leu Thr Arg Asn Gly Gln Thr Val
                420                 425                 430

Phe Ser Gly Thr Ser Leu Met Asp Ile Thr Asn Val Cys Ser Cys Gly
                435                 440                 445

Ile Tyr Asn Phe Asn Pro Tyr Val Gly Thr Ile Pro Ala Gly Phe Asp
450                 455                 460

Asp Pro Leu Gln Ala Asp Gly Leu Phe Ser Leu Thr Ile Gly Leu His
465                 470                 475                 480

Val Thr Thr Cys Gln Ala Lys Pro Ser Leu Gly Thr Asn Pro Pro Val
                485                 490                 495

Thr Ser Gly Pro Val Ser Ser Leu Pro Ala Ser Ser Thr Thr Arg Ala
                500                 505                 510

Ser Ser Pro Pro Pro Val Ser Ser Thr Arg Val Ser Ser Pro Pro Val
                515                 520                 525

Ser Ser Pro Pro Val Ser Arg Thr Ser Ser Ala Pro Pro Pro Ala
530                 535                 540

Ser Ser Thr Pro Pro Ser Gly Gln Val Cys Val Ala Gly Thr Val Ala
545                 550                 555                 560

Asp Gly Glu Ser Gly Asn Tyr Ile Gly Leu Cys Gln Phe Ser Cys Asn
                565                 570                 575

Tyr Gly Tyr Cys Pro Pro Gly Pro Cys Lys Cys Thr Ala Phe Gly Ala
                580                 585                 590

Pro Ile Ser Pro Pro Ala Ser Asn Gly Arg Asn Gly Cys Pro Leu Pro
                595                 600                 605

Gly Glu Gly Asp Gly Tyr Leu Gly Leu Cys Ser Phe Ser Cys Asn His
    610                 615                 620

Asn Tyr Cys Pro Pro Thr Ala Cys Gln Tyr Cys
625                 630                 635

<210> SEQ ID NO 2
<211> LENGTH: 2069
<212> TYPE: DNA
<213> ORGANISM: Trichoderma harzianum

<400> SEQUENCE: 2
atgttgggcg ttttccgccg cctcgggctg ggcgccctag ctgccgcagc tctatcttct     60
ctcggcagtg ccgctcccgc caatgttgct atccggtctc tcgaggagcg cgcttcctct    120
gctgaccgtc ttgtattctg tcacttcatg gttagttttt acctaggaat tataaggatg    180
aggactaatg tagcaacgtc atgacagatt ggtatcgttg gtgaccgtgg cagctcggca    240
gattatgatg acgatatgca acgtgccaaa gccgctggca ttgacgcctt cgccctgaac    300
atcggcgttg acggctatac cgaccagcag ctcggctatg cctatgactc tgccgatcgt    360
aatggcatga aagtcttcat ttcatttgat ttcaactggt ggagccccgg caatgcagtt    420
ggtgttggcc agaagattgc gcagtatgcc aaccgccctg cccagctgta tgtcgacaac    480
cggccattcg cctcttcctt cgccggtgac ggtctggatg taaatgcgtt cgctctgct    540 gcaggctcca acgtttactt tgtgcccaac ttccaccctg tcaatcttc ccctccaac     600
```

```
attgatggcg cccttaactg gatggtaagc cgcaactcca gagccgagag taggaaagca    660
atactaatgt gtttttaggc ctgggataat gatggaaaca acaaggcacc caagccgggc    720
cagactgtca cagtggcaga cggtgacaac gcttataaga attggttggg tggcaagcct    780
tacctggcgc ctgtctcacc ttggttttc acccatttcg gccccgaagt ttcatattcc    840
aagaactggg ttttcccagg tggtcctctg atctataacc ggtggcaaca ggtcttgcag    900
cagggtttcc ccatggttga gatcgttacc tggaatgact acggcgagtc tcactacgtc    960
ggtcccctga agtctaagca tttcgatgat ggcaactcca aatgggtcaa tgatatgccc   1020
catgatggat ccttgatct ttcgaagccg ttcattgcag catataagaa cagggatacc   1080
gacatctcca agtatgttca aaatgagcag cttgtttact ggtaccgccg caacttgaag   1140
gcattggact gcgacgccac cgacaccacc tctaaccgcc cggctaacaa tggaagcggt   1200
aattacttta tgggacgccc tgatggttgg caaactatgg atgacaccgt ttatgttgcc   1260
gcacttctca agactgccgg tagcgtcacg gtcacgtctg gtggcaccac tcaaacgttc   1320
caggccaacg ccggagccaa tctcttccaa atcccggcca gcatcggcca gcaaaagttt   1380
gctctgactc gtaacggtca gaccgtcttt agcggaacct cattgatgga tatcaccaac   1440
gtttgctctt gcggtatcta caacttcaac ccatatgttg gcaccattcc tgccggcttt   1500
gacgaccctc ttcaggctga cggtcttttc tctttgacca tcggattgca cgtcacaact   1560
tgtcaggcca agccatctct tggaactaac cctcctgtca cttccggccc tgtgtcctcg   1620
cttccagctt cctccaccac ccgcgcatcc tcgccgcctc ctgtttcttc aactcgtgtc   1680
tcttctcccc ctgtctcttc ccctccagtt tctcgcacct tttctgcccc tcccctccg    1740
gccagcagca cgccgccatc gggtcaggtt tgcgttgccg gcaccgttgc cgacggcgag   1800
tctggcaact acatcggcct gtgccaattc agctgcaagt aggttgcccc catacccctt   1860
acttgcttcc ttaactaatc ctttgtagct acggttactg cccaccagga ccgtgtaagt   1920
gcaccgcctt tggtgctccc atctcgccac cggcatccaa cggccgcaac ggctgccctc   1980
tgccgggaga aggcgatggt tatctgggcc tgtgcagttt cagttgtaac cataattact   2040
gcccgccaac ggcatgtcaa tactgctag                                      2069

<210> SEQ ID NO 3
<211> LENGTH: 1908
<212> TYPE: DNA
<213> ORGANISM: Trichoderma harzianum

<400> SEQUENCE: 3
atgttgggcg ttttccgccg cctcgggctg ggcgccctag ctgccgcagc tctatcttct     60
ctcggcagtg ccgctcccgc caatgttgct atccggtctc tcgaggagcg cgcttcctct    120
gctgaccgtc ttgtattctg tcacttcatg attggtatcg ttggtgaccg tggcagctcg    180
gcagattatg atgacgatat gcaacgtgcc aaagccgctg gcattgacgc cttcgccctg    240
aacatcggcg ttgacggcta taccgaccag cagctcggct atgcctatga ctctgccgat    300
cgtaatggca tgaaagtctt catttcattt gatttcaact ggtggagccc cggcaatgca    360
gttggtgttg gccagaagat tgcgcagtat gccaaccgcc ctgcccagct gtatgtcgac    420
aaccggccat cgcctcttc cttcgccggt gacggtctgg atgtaaatgc gttgcgctct    480
gctgcaggct ccaacgttta ctttgtgccc aacttccacc ctggtcaatc ttcccctcc    540
aacattgatg gcgcccttaa ctggatggcc tgggataatg atggaaacaa caaggcaccc    600
aagccgggcc agactgtcac agtggcagac ggtgacaacg cttataagaa ttggttgggt    660
```

```
ggcaagcctt acctggcgcc tgtctcacct tggtttttca cccatttcgg ccccgaagtt    720
tcatattcca agaactgggt tttcccaggt ggtcctctga tctataaccg gtggcaacag    780
gtcttgcagc agggtttccc catggttgag atcgttacct ggaatgacta cggcgagtct    840
cactacgtcg gtcccctgaa gtctaagcat ttcgatgatg gcaactccaa atgggtcaat    900
gatatgcccc atgatggatt ccttgatctt tcgaagccgt tcattgcagc atataagaac    960
agggataccg acatctccaa gtatgttcaa aatgagcagc ttgtttactg gtaccgccgc   1020
aacttgaagg cattggactg cgacgccacc gacaccacct ctaaccgccc ggctaacaat   1080
ggaagcggta attactttat gggacgccct gatggttggc aaactatgga tgacaccgtt   1140
tatgttgccg cacttctcaa gactgccggt agcgtcacgg tcacgtctgg tggcaccact   1200
caaacgttcc aggccaacgc cggagccaat ctcttccaaa tcccggccag catcggccag   1260
caaaagtttg ctctgactcg taacggtcag accgtcttta gcggaacctc attgatggat   1320
atcaccaacg tttgctcttg cggtatctac aacttcaacc catatgttgg caccattcct   1380
gccggctttg acgaccctct tcaggctgac ggtctttttct ctttgaccat cggattgcac   1440
gtcacaactt gtcaggccaa gccatctctt ggaactaacc ctcctgtcac ttccggccct   1500
gtgtcctcgc ttccagcttc ctccaccacc cgcgcatcct cgccgcctcc tgtttcttca   1560
actcgtgtct cttctccccc tgtctcttcc cctccagttt ctcgcacctc ttctgcccct   1620 cccctccgg ccagcagcac gccgccatcg ggtcaggttt gcgttgccgg caccgttgcc   1680
gacggcgagt ctggcaacta catcggcctg tgccaattca gctgcaacta cggttactgc   1740
ccaccaggac cgtgtaagtg caccgccttt ggtgctccca tctcgccacc ggcatccaac   1800
ggccgcaacg gctgccctct gccgggagaa ggcgatggtt atctgggcct gtgcagtttc   1860
agttgtaacc ataattactg cccgccaacg gcatgtcaat actgctag            1908

<210> SEQ ID NO 4
<211> LENGTH: 34
<212> TYPE: DNA
<213> ORGANISM: Artificial Sequence
<220> FEATURE:
<223> OTHER INFORMATION: primer

<400> SEQUENCE: 4
atataggcct atgttgggcg ttttccgccg cctc                                34

<210> SEQ ID NO 5
<211> LENGTH: 36
<212> TYPE: DNA
<213> ORGANISM: Artificial Sequence
<220> FEATURE:
<223> OTHER INFORMATION: primer

<400> SEQUENCE: 5
atatgcggcc gcctagcagt attgacatgc cgttgg                              36
```